US011518967B2

(12) United States Patent
Oberwalder

(10) Patent No.: US 11,518,967 B2
(45) Date of Patent: Dec. 6, 2022

(54) CHLORINE DIOXIDE DISINFECTING CLOTH

(71) Applicant: ALETHIA LIFE SCIENCES AG, Widnau (CH)

(72) Inventor: Sebastian Oberwalder, Munich (DE)

(73) Assignee: ALETHIA LIFE SCIENCES AG, Widnau (CH)

( * ) Notice: Subject to any disclaimer, the term of this patent is extended or adjusted under 35 U.S.C. 154(b) by 0 days.

(21) Appl. No.: 16/308,152

(22) PCT Filed: Jun. 9, 2017

(86) PCT No.: PCT/EP2017/064101
§ 371 (c)(1),
(2) Date: Dec. 7, 2018

(87) PCT Pub. No.: WO2017/212024
PCT Pub. Date: Dec. 14, 2017

(65) Prior Publication Data
US 2019/0218486 A1    Jul. 18, 2019

(30) Foreign Application Priority Data
Jun. 10, 2016    (DE) ...................... 10 2016 007 081.1

(51) Int. Cl.
| | |
|---|---|
| *C11D 17/04* | (2006.01) |
| *C11D 3/48* | (2006.01) |
| *C11D 3/395* | (2006.01) |
| *C11D 11/00* | (2006.01) |
| *A61L 2/232* | (2006.01) |
| *A61L 2/18* | (2006.01) |
| *C11D 3/04* | (2006.01) |
| *D21H 21/36* | (2006.01) |

(52) U.S. Cl.
CPC .............. *C11D 17/049* (2013.01); *A61L 2/18* (2013.01); *A61L 2/232* (2013.01); *C11D 3/042* (2013.01); *C11D 3/3951* (2013.01); *C11D 3/3953* (2013.01); *C11D 3/48* (2013.01); *C11D 11/0023* (2013.01); *D21H 21/36* (2013.01); *A61L 2202/11* (2013.01); *A61L 2202/17* (2013.01); *A61L 2202/24* (2013.01)

(58) Field of Classification Search
CPC ......... C11D 17/049; C11D 3/48; C11D 3/395; C11D 3/3951
See application file for complete search history.

(56) References Cited

U.S. PATENT DOCUMENTS

| | | | | |
|---|---|---|---|---|
| 3,634,183 A * | 1/1972 | Viola | ................... | A61K 8/0208 428/215 |
| 5,126,070 A | 6/1992 | Leifheit et al. | | |
| 6,325,969 B1 * | 12/2001 | Aamodt | .................. | A61L 2/186 422/28 |
| 6,866,145 B2 * | 3/2005 | Richards | ................. | A47L 13/17 206/219 |
| 7,303,737 B2 * | 12/2007 | Hemker | ................ | C01B 11/024 423/477 |
| 8,066,444 B2 * | 11/2011 | Rippl | ....................... | A47L 13/17 401/133 |
| 8,668,779 B2 * | 3/2014 | Cooper | ................... | A61L 9/145 134/22.12 |
| 9,433,474 B2 | 9/2016 | Swinney | | |
| 2004/0065315 A1 * | 4/2004 | Fish | ......................... | A61F 7/03 126/263.08 |

(Continued)

FOREIGN PATENT DOCUMENTS

| | | | | |
|---|---|---|---|---|
| JP | 2005255657 A | * | 9/2005 | ............. A01N 59/00 |
| WO | 2005107823 A1 | | 11/2005 | |

(Continued)

OTHER PUBLICATIONS

Translation of JP2005255657A from Espacenet (Year: 2019).*
Google Patent Search 'cloth containing chlorine dioxide' Oct. 22, 2019 (Year: 2019).*
Google Patent Search 'sheet impregnated with dry sodium chlorate' (Year: 2019).*
Google Patent Search 'cloth containing chlorite chlorine dioxide'-silicate (Year: 2019).*
Google patent search_package for cleaning product 2 solutions twist to activate_Jun. 8, 2020 (Year: 2020).*

(Continued)

*Primary Examiner* — Michael P Cohen
(74) *Attorney, Agent, or Firm* — The H.T. Than Law Group

(57) ABSTRACT

The invention relates to highly effective disinfecting or sterilising cloths with chlorine dioxide as the main active ingredient. For this, the chlorine dioxide is only generated shortly before use by bringing a cloth impregnated with a chlorite or chlorate salt in contact with a clearly defined amount of a suitable activation agent that is fluid or dissolved or admixed in a fluid, and prepackaged as a single dose, for the generation of chlorine dioxide. In a preferred embodiment, the impregnated cloth and the activation fluid are packaged in a common packaging unit and the activation occurs by breaking through a barrier separating the cloth or the cloths and the activation fluid. In a further preferred embodiment, the packaging is a moulded part having two packaging spaces separated from one another by removable barriers, which can be converted into a moulded part with only one chamber via simple pressure in one direction. The activation fluid or the disinfecting cloth can contain further substances, such as the pH-value-controlling substances, surfactants, guanidine derivatives, aldehydes, phenoxyethanols, phosphate esters, alcohols, sulfoxides, etc. Preferably, the disinfecting cloth according to the invention is used for disinfecting and/or sterilising medical instruments and/or medical products and/or surfaces.

14 Claims, No Drawings

(56) References Cited

U.S. PATENT DOCUMENTS

| | | |
|---|---|---|
| 2006/0051266 A1 | 3/2006 | Green et al. |
| 2007/0141126 A1* | 6/2007 | Hudson .............. A41D 31/0077 |
| | | 424/443 |
| 2007/0145328 A1* | 6/2007 | Boulanger ........... A61K 9/0019 |
| | | 252/187.21 |
| 2008/0127994 A1 | 6/2008 | Rippl et al. |
| 2014/0142489 A1 | 5/2014 | Green |
| 2017/0119916 A1 | 5/2017 | Richardson |

FOREIGN PATENT DOCUMENTS

| | | | |
|---|---|---|---|
| WO | WO-2007066865 A1 * | 6/2007 | ............. A47K 10/32 |
| WO | 2016102606 A1 | 6/2016 | |

OTHER PUBLICATIONS

Compressed_sponge_dispenser_expands_when_wet_-_Google_Patents_12-20-2021.pdf (Year: 2021).*

Wipe_pops_up_when_wet_-_Google_Search_12-19-21.pdf (Year: 2021).*

International Search Report and Written Opinion issued in connection with the corresponding International Application No. 2017/064101 dated Sep. 20, 2017.

* cited by examiner

CHLORINE DIOXIDE DISINFECTING CLOTH

The present invention relates to highly effective disinfection or sterilization cloths.

There is a great need for highly effective disinfection cloths and sterilization cloths, especially in the laboratory and medical sector. Examples of these are the sterilization of medical devices that cannot be autoclaved, for example endoscopes, and the cleaning of medical technology and laboratory equipment. In the cleaning of such devices, conventional disinfection cloths are often unsuitable owing to the limited or slow efficacy of the disinfectants used. This is especially true of alcohol, probably the most widely used disinfectant, which requires a relatively long contact time, but this is generally not achieved owing to vaporization.

As far as we know, just a single system to date achieves satisfactory efficacy by using chlorine dioxide as active ingredient; see, for example, WO2005107823, and US2014142489 and WO2015040366. Owing to the low stability of the chlorine dioxide active ingredient, the system described therein works by producing the active ingredient directly on use in that an activator spray is sprayed onto the preimpregnated wiping cloths and they are thus activated. This produces the chlorine dioxide required directly prior to use, and therefore the problem of storage stability is largely solved. However, the use of an activator spray to be operated manually leads in turn to another problem, namely the difficulty of the correct dosage of the activator. Owing to the variability in manual operation, this problem can only be solved to some degree in that the activator is always used in an excess dose. However, the effect of this is in turn that significant residues of the activator remain on the disinfected surface, and therefore recleaning of these surfaces is required to remove the excess activator.

However, this constitutes a significant problem for several reasons: more particularly, the recleaning operation with a now no longer sterilizing cloth can cause new contamination, which defeats the purpose of the prior sterilization, and reliable use of the system is actually no longer assured. A further operating step is likewise necessary, which, as well as new sources of error, in particular entails not inconsiderable additional time demands, and added costs both with regard to material and working time.

The present invention solves the problem in that the disinfection cloth impregnated with a component necessary for the production of chlorine dioxide is activated by contacting the disinfectant cloth with a clearly defined amount of an activating agent in liquid form that has been prepacked as a single dose. This allows the amounts of the impregnation and the activator in each case to be matched accurately in the required stoichiometric ratio, or the excess of one component to be sufficiently small as to no longer require recleaning for removal of the excess of one component.

In principle, all chlorite or chlorate salts are useful as impregnation for the cloth, preferably sodium chlorite, sodium chlorate, potassium chlorite, potassium chlorate, ammonium chlorite or ammonium chlorate. Suitable activating agents for production of chlorine dioxide are in principle all known co-reactants for production of chlorine dioxide, preferably an agent from Group 1:
  acids, further preferably: hydrochloric acid, sulfuric acid, phosphoric acid, peroxyacetic acid, carboxylic acids having an organic radical of C1-C40;
  persulfates;
  peroxodisulfates;
  perborates;
  percarbonates;
  peroxodicarbonates;
  permanganates, further preferably potassium permanganate;
  hypochlorites, further preferably sodium hypochlorite, potassium hypochlorite;
  iodine
  and/or hydrogen peroxide,
more preferably hydrochloric acid, peroxodisulfuric acid, phosphoric acid or hydrogen peroxide.

The activation liquid may in principle be packed in any form suitable for a single dose, preferably in a capsule or pouch. Useful packaging materials include all materials suitable for storage of the activating agent chosen, but preference is given to commercial plastics such as, in particular, polyethylene (PE), polypropylene (PP), polyvinyl chloride (PVC), polyamides (PA), polytetrafluoroethylene (PTFE) and polyurethanes (PU).

In a preferred embodiment, the capsule or pouch is packed together with an impregnated cloth in a liquid-tight outer package, preferably a commercial individual sachet package, Moreover, the capsule or pouch is configured in such a way that, when moderate manual pressure is exerted on one side or the upper end, the outer package bursts and, as a result, the activation liquid packed therein flows onto the cloth included in the package and is absorbed thereby, while the outer package remains intact. Thus, the activation reaction can proceed within the outer package isolated from the environment, and then, after it has concluded, the cloth that has now been impregnated with a chlorine dioxide solution can be removed from the outer package, for example by tearing open the sachet. Rather than one cloth, it is also possible for multiple cloths to packed in the same package, for example 10-100 cloths in a wrapper made of polymer film with a removal opening (multipack), or 50-500 cloths in a hard plastic packing with a removal opening (drum/bucket/dispenser).

In another preferred embodiment, the activation liquid and the impregnated cloth are packed together in a plastic trough, but are separated by a removable or penetrable barrier. This trough is closed at the upper end by a liquid-tight film. The separation barrier can then be pulled away when a liquid-tight closure film is pulled away, as a result of which the activation liquid then flows toward the impregnated cloth and is absorbed thereby, and hence the reaction of the components to give chlorine dioxide takes place. Alternatively, the barrier can be penetrated in the closed state, for example by pressure on the closure film, which results in the confluence and absorption or the reaction of the components to give chlorine dioxide still within the closed package.

In a further preferred embodiment, the package is a molded article having two separated package chambers which is converted to a molded article having just a single chamber by simple pressure or pulling in one direction. In this case, the impregnated cloth is in one chamber and the activation liquid in the other chamber. If the molded article is then shaped to give a single chamber by pressure or pulling, cloth and activator come into contact, and the reaction to give chlorine dioxide takes place. Prior to deformation by pressure or pulling, the molded article may also contain more than two chambers, which may be advantageous when, as well as the chemical for production of chlorine dioxide, further components are to be applied to the cloth in situ shortly prior to use.

In a particularly preferred embodiment, the molded article just described is executed in plastic, preferably PE, PP, PA, PVC, PTFE or PU, and is closed on one side solely with a removable or penetrable membrane, preferably likewise made of one of the plastics mentioned or of paper.

In a further-preferred execution, in the molded plastics article closed with a membrane that has just been described, a compressed, dry disinfection cloth made of an absorptive material, preferably cellulose, is packed, which increases its volume by at least 50% compared to dry storage as a result of contact with the activator liquid. Further preferably, the disinfection cloth of such increased size thus expands beyond the package and can thus be removed easily.

For better control of the reaction, the disinfection cloth and/or the activation liquid, in a preferred embodiment, additionally contain one or more pH-regulating substances, preferably a carbonate, hydrogencarbonate, sulfate, hydrogensulfate, phosphate and/or hydrogenphosphate, either as an addition to the liquid and/or as additional impregnation. For handling reasons, preference is given to an addition to the liquid, and it is also possible for one or more substances to be present in the liquid to improve the mixing/distribution, while one or more substances may be used alternatively or additionally as impregnation.

In a further preferred embodiment, the disinfection cloth and/or the activation liquid additionally contain one or more surfactants, preferably a quaternary ammonium compound or a nonorganic surfactant, either as an addition to the liquid and/or as additional impregnation. For reasons of handling, preference is likewise given here to an addition to the liquid, and it is also possible for one or more substances to be present in the liquid to improve the mixing/distribution, while one or more substances may be used alternatively or additionally as impregnation. The substances mentioned can further increase the disinfectant action and/or improve the distribution of the chlorine dioxide on the article to be disinfected or the surface to be disinfected. The surfactants can likewise slow the escape of the chlorine dioxide from the liquid, and hence contribute to avoiding or reducing any pollution of the environment or endangerment of the user. By virtue of the substances coming into contact with chlorine dioxide only briefly because it is produced only shortly prior to use by contact of the activation liquid with the impregnation, the interaction of these substances with the chlorine dioxide is only minor. More particularly, there is only slight mutual degradation, and therefore the common use of these substances with chlorine dioxide in the present context is possible in an unproblematic manner.

In a further preferred embodiment, the disinfection cloth and/or the activation liquid additionally contain one or more substances from the following group 2:
guanidinium derivatives, especially PHMB;
aldehydes, especially glutaraldehyde;
phenols, especially chloroxylenol, triclosan;
chlorhexidine;
octenidine;
phenoxyethanols;
and/or phosphate esters, preferably ethoxylated aliphatic-phosphate esters or phosphate diesters and/or alkyl ether phosphates,
either as an addition to the liquid and/or as additional impregnation. For reasons of handling, preference is likewise given here to an addition to the liquid, and it is also possible for one or more substances to be present in the liquid to improve the mixing/distribution, while one or more substances may be used alternatively or additionally as impregnation. The substances mentioned can further increase the disinfectant action and/or improve the distribution of the chlorine dioxide on the article to be disinfected or the surface to be disinfected and/or, as well as the short-term disinfecting action, ensure additional medium- or long-term antimicrobial efficacy. By virtue of the substances coming into contact with chlorine dioxide only briefly because it is produced only shortly prior to use by contact of the activation liquid with the impregnation, and then evaporates or outgases relatively rapidly from the surface, the interaction of these substances with the chlorine dioxide is only minor. More particularly, there is only slight mutual degradation, and therefore the common use of these substances with chlorine dioxide in the present context is possible in an unproblematic manner.

In a further preferred embodiment, the activation liquid contains, as solvent and/or as additional ingredient, one or more substances from the following group 3:
water;
alcohols, especially ethanol and isopropanol;
ketones, especially acetone;
sulfoxides, especially DMSO;
and/or carboxylic esters, especially ethyl acetate.

These substances lead in particular to better dissolution and distribution of the ingredients. In addition, they can also improve the distribution of the chlorine dioxide on the article to be disinfected or the surface to be disinfected and/or further increase the disinfectant action. Moreover, they can increase the depth of penetration of the disinfectant into the surface treated. By virtue of the substances coming into contact with chlorine dioxide only briefly because it is produced only shortly prior to use by contact of the activation liquid with the impregnation, the interaction of these substances with the chlorine dioxide is only minor. More particularly, there is only slight mutual degradation, and therefore the common use of these substances with chlorine dioxide in the present context is possible in an unproblematic manner.

In addition, the activation liquid may contain a color indicator which causes the disinfection cloth to change color on contact. For this purpose, the disinfection cloth may be packed wholly or partly under a transparent package surface. The indicator substance may also be present as impregnation in the disinfection cloth, and be activated on contact with liquid. More preferably, the indicator liquid is simultaneously a chemical indicator for the presence of chlorine dioxide, e.g. potassium iodide dissolved in sulfuric acid, where there is a color change on contact with chlorine dioxide (iodide-iodine reaction).

Preferably, the above-described disinfection cloth, no matter how it is designed, is used for disinfection and/or sterilization of medical instruments and/or medical products and/or laboratory equipment and/or surfaces, preferably in: hospitals and/or doctors' practices and/or laboratories, especially laboratories with safety level 2 or higher.

The invention claimed is:

1. A disinfection cloth, that is activated prior to use by contacting
   A.) a dry cloth impregnated with a chlorite or chlorate salt, with
   B.) a defined amount, prepacked as a single dose, of an activation liquid, wherein the activation liquid is an activating agent in a liquid state or comprises an activating agent that has been admixed or dissolved in a liquid, for generation of chlorine dioxide, wherein the impregnated cloth and the activation liquid are packaged in a common package unit being an initially closed molded article which has two or more package chambers separated by one or more removable barriers and can be converted to a molded article having just one chamber and wherein the impregnated cloth comprises an absorptive material which is in dry and in folded and/or pressed form and increases its volume as a result of contact with the activation liquid, so that the disinfection cloth of such increased size expands beyond the common package unit.

2. The disinfection cloth as claimed in claim 1, wherein the one-chamber molded article resulting from applying the pressure or pulling contains an openable or penetrable packaging membrane on one side of the molded article.

3. The disinfection cloth as claimed in claim 1, wherein the activation liquid additionally contains one or more pH-regulating substances, and/or the impregnated cloth has additionally been impregnated with said one or more pH-regulating substances.

4. The disinfection cloth as claimed in claim 3, wherein the pH-regulating substances are selected from a carbonate, a hydrogen carbonate, a sulfate, a hydrogensulfate, a phosphate and a hydrogenphosphate.

5. The disinfection cloth as claimed in claim 1 wherein either the activation liquid additionally contains one or more surfactants, and/or the impregnated cloth has additionally been impregnated with said one or more surfactants.

6. The disinfection cloth as claimed in claim 5, wherein the surfactants are selected from a quaternary ammonium compound and a nonorganic surfactant.

7. The disinfection cloth as claimed in claim 1, wherein either the activation liquid additionally contains one or more substances from the following group 2:
guanidinium derivatives, or PHMB;
aldehydes, or glutaraldehyde;
phenols, chloroxylenol, triclosan;
chlorhexidine;
octenidine;
phenoxyethanols;
and/or phosphate esters, ethoxylated aliphatic phosphate esters or phosphate diesters and/or alkyl ether phosphates,
and/or the impregnated cloth has instead or additionally been impregnated with one or more substances from this group 2.

8. The disinfection cloth as claimed in claim 7, wherein the phosphate esters are selected from a group consisting of ethoxylated aliphatic phosphate esters or phosphate diesters and/or alkyl ether phosphates.

9. The disinfection cloth as claimed in claim 1, wherein the activating agent had been dissolved in and/or admixed with a substance from the following group 3:
water;
alcohols, or ethanol or isopropanol;
ketones, or acetone;
sulfoxides, or DMSO;
and/or carboxylic esters, or ethyl acetate.

10. The disinfection cloth as claimed in claim 1, wherein the chlorite or chlorate salt is selected from sodium chlorite, sodium chlorate, potassium chlorite, potassium chlorate, ammonium chlorite and ammonium chlorate.

11. The disinfection cloth as claimed in claim 1, wherein the activating agent is selected from hydrochloric acid, peroxodisulfuric acid, phosphoric acid and an oxidizing agent.

12. The disinfection cloth as claimed in claim 1, wherein the chlorite or chlorate salt impregnating the cloth and the activating agent are substantially in stoichiometric ratio.

13. A disinfection cloth, that is activated prior to use by contacting
A.) a dry cloth impregnated with a chlorite or chlorate salt, with
B.) a defined amount, prepacked as a single dose, of an activation liquid, wherein the activation liquid is an activating agent in a liquid state or comprises an activating agent that has been admixed or dissolved in a liquid, for generation of chlorine dioxide,
wherein the impregnated cloth and the activation liquid are packaged in a common package unit being an initially closed molded article which has two or more package chambers separated by one or more removable barriers and can be converted to a molded article having just one chamber and
wherein the impregnated cloth comprises an absorptive material which is in dry and in folded and/or pressed form and increases its volume as a result of contact with the activation liquid, so that the disinfection cloth of such increased size expands beyond the common package unit,
wherein the impregnated cloth increases its volume by at least 50% compared to dry storage as a result of contact with the activation liquid.

14. A method for sterilizing medical instruments and/or medical products and/or surface comprising the step of contacting the disinfection cloth as claimed in claim 1 to said medical instruments and/or medical products and/or surfaces.

* * * * *